United States Patent [19]
Norlander

[11] Patent Number: 5,779,857
[45] Date of Patent: Jul. 14, 1998

[54] METHOD FOR THE PREPARATION OF DEFIBERED CELLULOSE PRODUCTS

[75] Inventor: Leif Norlander, Falun, Sweden

[73] Assignee: Stora Kopparbergs Bergslags Aktiebolaf, Falun, Sweden

[21] Appl. No.: 553,539

[22] PCT Filed: Jun. 21, 1994

[86] PCT No.: PCT/SE94/00613

§ 371 Date: Nov. 30, 1995

§ 102(e) Date: Nov. 30, 1995

[87] PCT Pub. No.: WO95/00703

PCT Pub. Date: Jan. 5, 1995

[30] Foreign Application Priority Data

Jun. 23, 1993 [SE] Sweden ................. 9302166

[51] Int. Cl.$^6$ .............. D21H 11/20; D21H 17/06; A61L 15/16
[52] U.S. Cl. .............. 162/157.6; 162/9; 162/182; 8/115.51; 8/116.1
[58] Field of Search ............... 162/157.6, 164.3, 162/158, 182, 9, 184, 173, 146; 604/375, 378, 379, 367; 8/116.1, 115.51, 184, 115.56, 116.4, 195, 185, 181

[56] References Cited

U.S. PATENT DOCUMENTS

| 3,224,926 | 12/1965 | Bernardin | 162/146 |
| 3,434,918 | 3/1969 | Bernardin | 162/111 |
| 4,853,086 | 8/1989 | Graef | 162/157.6 |
| 4,888,093 | 12/1989 | Dean et al. | 162/157.6 |
| 4,889,595 | 12/1989 | Herron et al. | 162/157.6 |
| 4,889,596 | 12/1989 | Schoggen et al. | 162/157.6 |
| 5,009,650 | 4/1991 | Bernardin | 604/378 |
| 5,124,197 | 6/1992 | Bernardin et al. | 428/284 |
| 5,366,591 | 11/1994 | Jewell | 162/9 |
| 5,384,012 | 1/1995 | Hazard, Jr. | 162/9 |

FOREIGN PATENT DOCUMENTS

WO 88/04704  6/1988  WIPO.

Primary Examiner—Donald E. Czaja
Assistant Examiner—Jose S. Fortuna
Attorney, Agent, or Firm—Nixon & Vanderhye

[57] ABSTRACT

Defibrated cellulose product comprising a fibrous structure having good compressibility under the influence of heat and pressure. The structure is obtained by cross-linking, in a dry state, cellulose fibers which are impregnated with cross-linking agent and at least one polyfunctional alcohol, and which a difibrated prior to carrying out the cross-linking reaction. The cross-linking reaction is carried out at an elevated temperature of at least 110° C.

16 Claims, 7 Drawing Sheets

METHOD FOR THE PREPARATION OF DEFIBERED CELLULOSE PRODUCTS

This application is a national stage application under 35 U.S.CX. 371 of International Application Number PCT/SE94/00613, filed Jun. 21, 1994.

TECHNICAL FIELD

The present invention relates to a defibrated cellulose product, in particular fluff pulp, containing crosslinked cellulose fibres. The invention also relates to an absorptive body which consists, at least in part, of the said cellulose product, and also to a method for preparing a cellulose pad, in particular fluff pulp, which method includes defibration, i.e. individualizing the cellulose fibres with mechanical devices and crosslinking them.

STATE OF THE ART

There has for many years been an interest in chemically crosslinked fluff pulp and it has been proposed that this pulp should be used in absorbent hygiene products. This proposal has been based, in particular, on the favourable properties of the crosslinked cellulose, particularly as regards absorption capacity, wet specific volume and absorption rate, which properties are particularly important when producing absorbent hygiene products such as nappies (diapers), sanitary towels, etc.

In U.S. Pat. No. 3,224,926 (1965), Bernadin has described the use of formaldehyde for crosslinking cellulose in the dry and defibrated condition. In addition, the use of other crosslinking reagents has been proposed by, inter alia, Schoggen et al., U.S. Pat. No. 879,678 (1986) (bifunctional aldehydes); Herron, Cooper, U.S. Pat. No. 432,648 (1989) (polyfunctional carboxylic acids); and Norlander, International Patent Application PCT/SE93/00086 (derivatives of dihydroxyethyleneurea). Defibrated cellulose, i.e. individualized cellulose fibres, for example fluff pulp, which is produced in accordance with these methods exhibits a consistent improvement in absorption capacity, wet specific volume and absorption rate.

In addition, PA Graef, WO 88/04704, has reported that a cellulose product produced by treating cellulose with polyfunctional aldehydes, as cellulose crosslinking agents, in the presence of ethylene glycols, propylene glycols or polyether glycols possesses improved absorption properties, principally absorption rate. The crosslinking reaction, if such a reaction takes place, is carried out in a conventional drying machine with the cellulose fibres being in sheet-form, i.e. in the presence of fibre-to-fibre bonds and at temperatures which must not exceed 100° C. The dry matter content associated with any crosslinking reaction which is carried out is stated to be 1–20 %, ie. the fibres are partially swollen by water. Sheet-fibrating is carried out in subsequent stages in a conventional manner in the dry state prior to shaping the absorptive bodies, which are designed to be used in babies' nappies, feminine products, etc. The increase in absorption capacity as compared with completely untreated fibres is reported to amount to approximately 15%.

A cellulose product having exposed, dry-crosslinked fibres is normally characterized by a high degree of resilience in the dry state, signifying that high pressures and high temperatures are required in order to compress the product to high densities, for example greater than 0.20–1.0 g/cm3. According to Sultze, PCT/US92/01668, pressures of between 800 and 115,000 psi (55–7930 bar) and temperatures of between 60° C. and 180° C. are needed in order to achieve this. For several reasons, the high degree of resilience represents a disadvantage. For instance, powerful, and consequently expensive, tools are required for compressing to high density.

BRIEF DISCLOSURE OF THE INVENTION

The object of the present invention is to make available a defibrated cellulose product of the type specified in the introduction, which product possesses a fibre structure having an improved, preferably controllable, compressibility. More particularly, the object of the invention is to make available a cellulose product for use in absorbent products, more particularly in absorbing pads designed to collect body fluids, for example those products which include babies' nappies, sanitary towels and incontinence products. An especial object in this context is to be able to make available absorbent products which are thinner and more comfortable—but which still possess good absorption properties—than has previously been possible.

A further object is to be able, by means of the improved compressibility, to utilize transport-vehicle and storage-space capacity more efficiently and to decrease transport and storage costs.

These and other objects can be achieved by the defibrated cellulose product according to the invention being characterized by possessing a fibre structure having an improved compressibility under the influence of heat and pressure, which structure can be obtained by crosslinking, in the dry state, cellulose fibres which are impregnated with an effective quantity of crosslinking agent and at least one bifunctional, trifunctional or polyfunctional alcohol and which are defibred prior to carrying out the crosslinking reaction. By carrying out the defibering before the crosslinking, the fibres can be individualized more efficiently than would be the case if the crosslinking were to be carried out before the defibration, i.e. good fluffing can be achieved.

The cellulose fibres are expediently crosslinked at a temperature of between 100° and 210° C., preferably at a temperature greater than 120° C., expediently between 140° and 210° C. Where appropriate, impregnating agents other than bifunctional, trifunctional or polyfunctional alcohols can also provide the effect in accordance with the invention, which effect is expressed by the product gaining a fibre structure having improved compressibility under the influence of heat and pressure. In this case, the use of such chemicals is also included in the invention. The said crosslinked cellulose fibres probably consist of swollen, and thereby softened, cellulose polymers, which can be obtained by impregnating the cellulose fibres with an effective quantity of bifunctional, trifunctional or polyfunctional alcohols or with some other preparation which causes the fibres to swell.

Another way of characterizing the product according to the invention is that, after having been compressed, it has a density which is at least 15% higher, under the same conditions as regards compression time, heat and pressure, than that of a cellulose product whose fibres have not been impregnated with bifunctional, trifunctional or polyfunctional alcohols or with any other preparation which causes the fibres to swell but whose fibres are otherwise of the same type, and are crosslinked with the same amount and agent, as the fibres in the cellulose product according to the invention.

The compressibility of the defibrated and crosslinked cellulose product, normally the fluff pulp, is affected by adding a bifunctional, trifunctional or polyfunctional alcohol, expediently together with the crosslinking reagent. The alcohols which are most suitable for use are those which have boiling points (at atmospheric pressure) which exceed the reaction temperature of the crosslinking reaction, i.e. alcohols having boiling points exceeding 100° C., preferably 120° C. and expediently exceeding 140° C.

A working hypothesis, formulated in this instance, regarding a probable chemical mechanism involves the hydroxyl groups of the polyfunctional alcohols reacting with the crosslinking reagent in the same way as do the hydroxyl groups of the cellulose. In this way, the alcohols are bound by covalent bonds to the cellulose molecule and the state of swelling of the latter is altered, in association with which the resilience is decreased in the dry state. The addition of alcohol appears to result in a form of softening of the crosslinked cellulose polymer, at least in the dry state and especially at high temperatures. The cellulose fibres which have been chemically crosslinked in this way can be compressed to a substantially higher density, at greatly reduced pressure, as compared with dry-crosslinked cellulose fibres to which none of the said alcohols has been added.

It should be pointed out in this connection that the said hypothesis is not intended to be of any delimiting significance for the scope and validity of the sought-after patent.

Chemicals other than the said alcohols which can cause the cellulose structure to swell can thus also be considered to fall within the scope of the concept of the invention.

Regardless of the correctness of the abovementioned working hypothesis, this invention makes available a method for preparing a cellulose product, especially fluff pulp, which method involves defibering the cellulose fibres and crosslinking the latter in the dry state, which preparation also provides the possibility of adjusting the compressibility of the finished product in advance. In accordance with the invention, the cellulose fibres are impregnated with an effective quantity of chemicals which are seen to cause the fibres to swell, and thereby soften the cellulose polymers, resulting in an improved compressibility of the cellulose product under the influence of heat and pressure. In this way, cellulose fibre structures are formed, at least in the presence of a high level of one of the said alcohols in the fibres, which can be compressed to the desired density at moderate pressures and temperatures, and which at the same time possess essentially unchanged absorption properties, as compared with crosslinked, conventionally prepared, fluff which has been compressed to the same density but using substantially higher pressure and temperature.

The fluff according to the present invention has a consistently higher absorption capacity and wet specific volume than does a corresponding pulp consisting of untreated, non-crosslinked cellulose fibres compared at the same initial dry density prior to wetting with liquid.

The ability to control the compressibility of a fluff pulp containing crosslinked cellulose fibres is very important when producing absorbent products, such as nappies, sanitary towels, incontinence products, etc. The obvious advantage of the defibered, crosslinked cellulose product according to the invention is that it can be compressed to high densities at moderate pressures and temperatures but nevertheless be given absorption properties which are equivalent to, or greater than, the corresponding properties of fibre structures which have been formed using non-crosslinked fibre having a substantially lower dry density.

For optimal use of the cellulose fibre, products according to the invention having density gradients, should probably be produced, for example by webs being formed and compressed to different densities prior to assembly, or by pulp having different compressibilities, for example as a result of varying the added quantity of bifunctional trifunctional or polyfunctional alcohols or equivalent chemicals for impregnating the cellulose fibres, being formed into air-laid or wet-laid webs and then compressed in a common press nip. In this way, an absorptive body can be formed having a density gradient. The number of layers which are used in the absorbent product, and the densities of the different layers, can be determined by the intended area of application. An upper layer of low density can be suitable for products which are to be loaded with large quantities of liquid over a short period of time, which upper layer can face the wearer of the absorbent product, while the layer(s) connected to it can be compressed to (a) higher density (densities).

A baby's nappy of the modern type is nowadays packed at an average density of 130–170 kg/m3. The pulp according to the invention provides excellent opportunities for increasing the average density of the absorptive body in absorbent products and thereby lowering the costs for transporting and storing these products.

The pulp according to the present invention can also be formed into fibre webs having a high density. The fibre webs can be formed using either a dry or a wet forming technique, with the fibres being dispersed in air or water in conjunction with the web being formed on an endless wire. These webs can be rolled into rolls having a high density, thereby substantially reducing the cost of transporting and storing the pulp as a semi-finished product. The fibre web can subsequently be defibrated, for example in a hammer mill, after which it can be formed into products having the desired density, which density can be substantially lower than the original density of the pulp and entirely dependent on the demands placed on the absorption properties of the final product. Alternatively, the web can be cut into pieces having the desired dimensions and placed directly in the desired position in the absorbent product. A very great advantage in this connection is that the pulp containing the dry-crosslinked cellulose fibres according to the invention can be used in the type of equipment which is nowadays available for producing nappies (also incontinence pads) as well as in machines for manufacturing sanitary towels and air-formed paper.

Webs which are formed out of a pulp according to the present invention can also, on being shaped, be provided with superabsorbent polymer (SAP) in the form of powder or fibres. In this instance, SAP are defined as polymers which can form gels containing at least 10 g of water per g of polymer. Certain applications might require strengthening of the fluff with the aid of long fibres which increase the tear strength. Examples of fibres having this effect are viscose fibres and polyester fibres, but other polymeric fibres can also be used. In this way, webs can be formed which are sufficiently strong to be incorporated in processes in which webs having a special density can be cut to size and placed in the desired position in absorbent products. Increased strength is also desirable for products having low surface weights, in order to ensure that the absorbing pad does not rupture in the final product.

Such strengthening fibres can also be of interest when manufacturing pulp webs which it is intended to defibrate in conventional defibrating equipment, for example in a hammer mill, for use at a density which is lower than the density of the original web. The reinforcing fibres then contribute to the creation of a fibre structure having a low density and good absorption properties together with substantially increased strength.

A bifunctional, trifunctional or polyfunctional alcohol having a molecular weight which exceeds 60 g/mol is expediently used for impregnating the fibres. Where appropriate, the carbon skeletons of the said alcohols can also contain heteroatoms, for example oxygen or nitrogen. The polyfunctional alcohols, or their equivalents, can also, where appropriate, contain one or two polar functional groups of the aldehyde, keto or carboxyl type.

In accordance with the invention, cellulose fibres are expediently impregnated with 2–150 g of bifunctional, trifunctional or polyfunctional alcohol/kg of cellulose fibres. The alcohol preferably consists of glycerol, which is supplied at 5–50 g/kg of cellulose fibre. On the one hand, glycerol is relatively cheap and, on the other, it does not have any toxic or sensitizing properties. Cellulose fibres for crosslinking can be selected from the bleached, partially bleached or unbleached, sulphate-delignified or sulphite-delignified, softwood or hardwood fibre groups. The cellulose fibre can also be selected from the thermomechanical and chemothermomechanical pulp groups.

The following process can be used when producing the dry-crosslinked and compressible fluff pulp. The cellulose fibres are impregnated with aqueous solutions containing the chemicals which are to be added. In this context, crosslinking agents are preferably used which are selected from one of the groups: bifunctional, trifunctional or polyfunctional organic acids, bifunctional trifunctional or polyfunc-tional aldehydes, derivatives of dihydroxyethyleneurea or derivatives of dimethyloldihydroxyethyleneurea. The quantity of crosslinking agent which is added to the cellulose fibres are adjusted within the interval 5–150 g of crosslinking agent/kg of cellulose fibres. The quantity of crosslinking agent is preferably adjusted to the interval 15–50 g of crosslinking agent/kg of cellulose fibre. The subsequent crosslinking can be catalyzed by so-called Lewis acids, for example iron(III) chloride, zinc(II) chloride or magnesium(II) chloride. In addition, substances selected from the groups: alkali metal hypophosphite, alkali metal polyphosphate, alkali metal phosphate, alkali metal sulphate, sodium fluoroborate, disodium carbonate and organic amines can catalyze all the abovementioned crosslinking reagents. The above-mentioned bifunctional, trifunctional or polyfunctional alcohols, or their equivalents, are also added to the said aqueous solution.

The cellulose fibre is then formed into a web which is dried at temperatures which are sufficiently low to ensure that the crosslinking reagent is not activated prior to the subsequent defibration which then takes place in the dry state, i.e. at a dry matter content which exceeds 80%, and is preferably between 90 and 95%. The dry fibration is expediently carried out using a hammer mill. Alternatively, the cellulose fibres are defibrated before the drying process, thus in the wet state, resulting in the cellulose fibre being twisted during drying, something which is well known from the manufacture of so-called flash-dried pulp. Defibration in the wet state is carried out at a dry matter content of 30–80%, preferably at 40–55%.

The defibrated and dried cellulose fibres are crosslinked, in the dry and individualized state, by the crosslinking reagent which has been added and being activated by means of heating to reaction temperature. The heating of the material preferably takes place by means of the individualized cellulose fibre being dispersed in hot air. The reaction temperatures which are required depend on the crosslinking reagent employed. In order to achieve technically acceptable reaction times, the reaction is expediently carried out at 140°–190° C. The crosslinking reaction is then carried out using a dwell time of between 1 and 30 minutes, preferably between 2 and 10 minutes.

Further characteristics and aspects, and also advantages, of the invention are evident from the subsequent patent claims and from the following account of experiments which have been carried out, and from the subsequent description of a preferred embodiment of the method according to the invention.

BRIEF DESCRIPTION OF THE FIGURES

In the following description of experiments which have been carried out, reference will be made to the attached drawings, of which

DESCRIPTION OF MEASUREMENT METHODS

Determination of specific volume and absorption properties in accordance with modified Scan-C 33:80

Definitions

Absorption capacity:

The ratio between the mass (weight) of the liquid which is taken up by a standard test sample of the fluff under defined conditions and the original mass (weight) of the test sample.

Specific volume:

Volume of the test piece in the dry state (dry specific volume) or in the wet state (wet specific volume) per unit mass (unit weight) of fluff.

For the measurements, test pieces of fluff are used which have a mass of 1.0 g and a diameter of 50 mm and which have been formed, by air forming, in pad form of the same type as is described in Scan-C 33:80. The density of the test pieces after forming is between 45 and 60 kg/m3.

Figure 1:
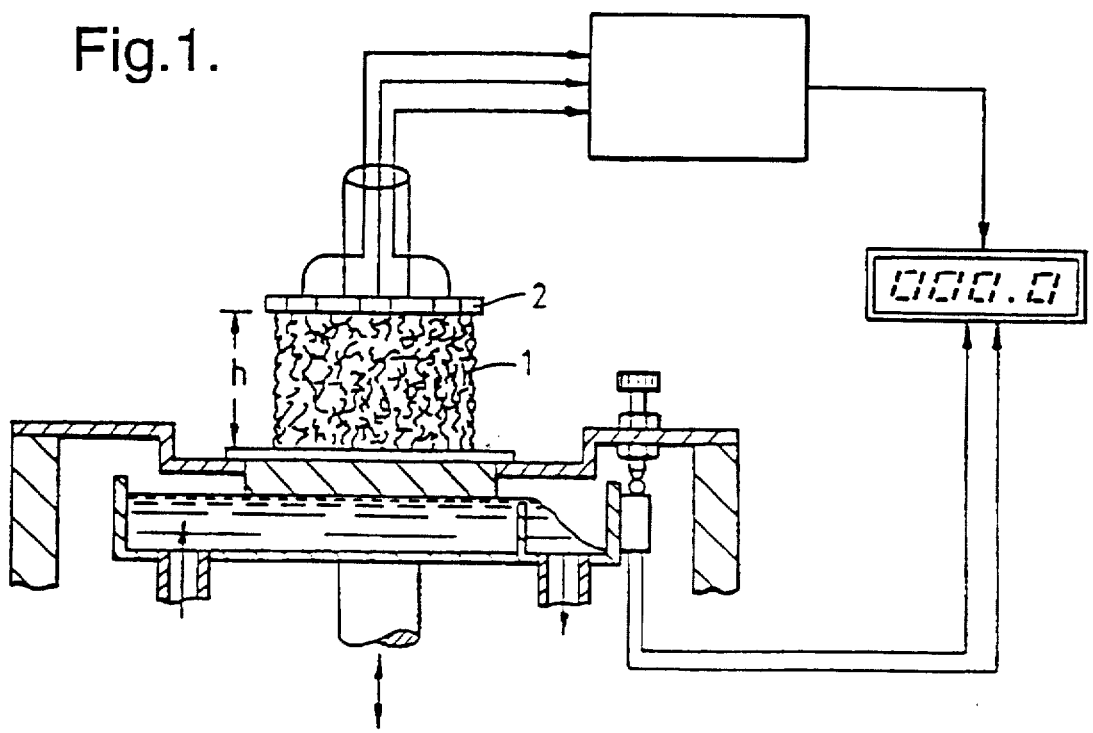
FIG. 1 shows how absorption properties and specific volume are determined in accordance with Scan-C 33:80.

The test pieces were compressed at different pressures and temperatures in a laboratory press having thermostatted press plates. The thickness of the test pieces was determined using a spring-loaded thickness gauge which loads the sample with 2.5 kPa on a circular surface area of 3.14 cm2. The thickness of the compressed test pieces was determined at least one hour after compressing, following conditioning at 23° C. and 50% RH. An apparatus of the type which is shown in FIG. 1 was used for the measurements. The test piece 1 is placed vertically and a weight 2 is placed on top of it, which weight loads the test pieces with a pressure of 2.5 kPa. The test piece is permitted to absorb water from below through a perforated bed 3. The water level is adjusted such that the underside of the test sample only just dips down into the water. The test sample is allowed to absorb water for 30 seconds, after which the water level is lowered. The test piece is then allowed to drain for 30 seconds, after which the weight 2 is removed and the wet test piece is weighed.

After weighing, the thickness of the test piece in the wet state is determined using a spring-loaded thickness gauge which loads the sample with 2.5 kPa on a circular surface area of 3.14 cm2. The reading is taken 30 seconds after the load has been applied.

The absorption capacity is calculated from the expression Y=(b−w)/w, where
Y=the absorption capacity in g/g
b =the mass of the wet test sample in g
The wet specific volume is calculated from the expression X=A×h×w, where
X=specific volume in dm3/kg
A=the surface area of the bottom of the test sample in cm2
w=the mass of the dry test sample in g
h=the height in cm of the test sample while being loaded in the dry state and the wet state, respectively.
The dry density is calculated from $$D = \frac{w}{A \times h} \times 1000 (kg/m3)$$

Determination of absorption rate (acquisition)

Figure 2:
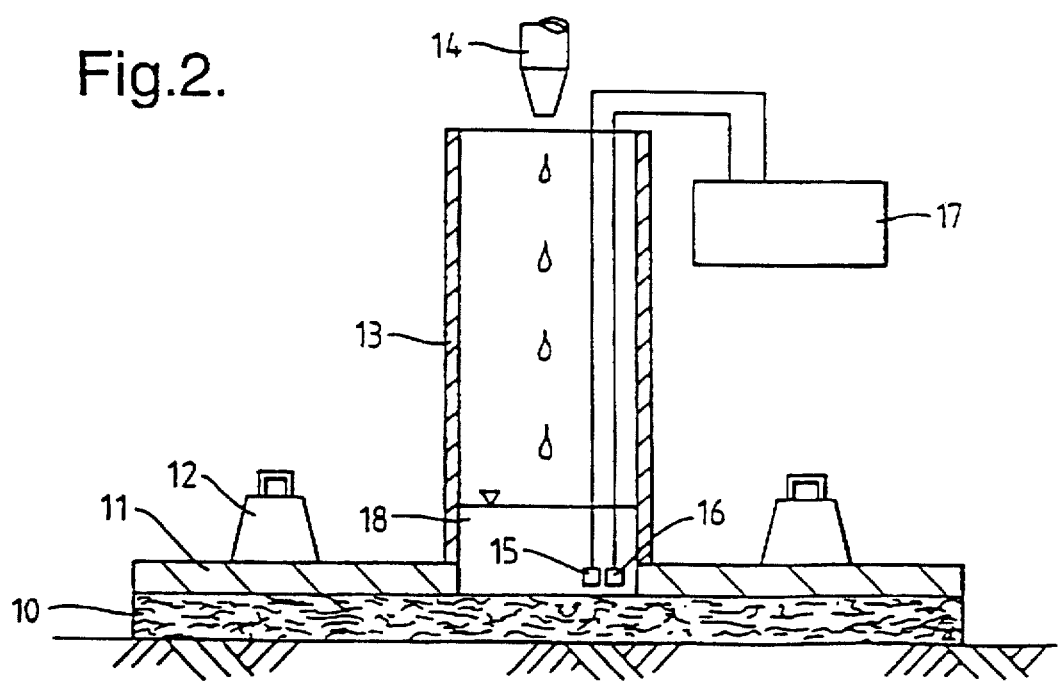
FIG. 2 illustrates a method for determining absorption rate (acquisition)

An apparatus which is shown schematically in FIG. 2 was used for these measurements. The sample 10 is covered with a non-woven, 17 g/m2 spun-bonded polypropene from Fibreweb and placed under a plate 11, which was loaded with weights 12 so that the sample 10 was subjected to a compression pressure of 2.6 kPa. The plate 12 has the same dimensions, 12*30 cm. as the sample 10. There is a circular hole in the rectangular plate and the hole is connected to a pipe 13 which has the same diameter, 50 mm. as the said hole. A metering hose has been designated 14; a pair of electrodes at the bottom of the pipe 13, immediately above the sample 10, have been designated 15, 16; and electronic and chronometric equipment has been designated 17.

Per liter, the synthetic urine contained: 9.0 g of NaCl 2.69 g of KH2PO4, approximately 1.8 g of Na2HPO4 and 0.1 g of acid fuchsin, with the remainder essential being distilled water. The pH of the liquid was 6.1–6.4.

50 ml of the liquid was metered down into the pipe 13 in 5 s from the metering hose 14. The liquid in the pipe has been designated 18. The time was measured which was taken for the sample to absorb and spread the liquid 18, i.e. the time it took to empty the pipe 13 of all liquid. Each test was carried out 4 times, i.e. 4 doses of synthetic urine were applied to the sample at 5 min intervals, with each dose consisting of 50 ml of synthetic urine.

EXPERIMENTAL SERIES 1

A4 sheets of fluff pulp of the bleached softwood sulphate type (STORA Fluff EC 0.1) were conditioned at 23° C. and 50% RH (relative humidity), and weighed. The sheets were impregnated with chemicals by dipping, for 15 s, into solutions having the composition given in Table 1.

The wet sheets were pressed, between absorbent paper, in a laboratory press to a dry matter content of a good 50%, at a sheet pressure of approximately 5 bar. The sheets were dried at 80° C. for 2 hours while being clamped under a dryer felt on a drying cylinder, after which drying of the sheets was completed by heating at 110° C. for 25 min. The dried sheets were weighed and the amount of chemicals applied (amount added per amount of cellulose) was calculated.

The impregnated sheets were conditioned at 50% RH and 23° C. for 4 hours, and were then defibrated in a Kamas HO1 hammer mill at 4500 revolutions/min, so that the fibres were substantially individualized. The defibrated material was heated up to the reaction temperature in a warm-air oven in which thermostatted air is blown through a bed of the material The defibrated material was kept in the oven at the reaction temperature for 6 min.

TABLE 1

| Sample No. | Crosslinking agent citric acid g/l | Catalyst disodium hydrogen phosphate g/l | Impregnating agent alcohol A[1] g/l | B[2] g/l | C[3] g/l | D[4] g/l | Total amount applied g/kg |
|---|---|---|---|---|---|---|---|
| 1:0 | 50 | 19 | — | — | — | — | 62 |
| 1:2 | 50 | 19 | 19 | — | — | — | 79 |
| 1:3 | 50 | 19 | 63 | — | — | — | 115 |
| 1:4 | 50 | 19 | — | 63 | — | — | 114 |
| 1:5 | 50 | 19 | — | — | 63 | — | 120 |
| 1:6 | 50 | 19 | — | — | — | 63 | 123 |
| 1:10[5] | | | | | | | 0 |

[1])Alcohol A = glycerol
[2])Alcohol B diethylene glycol
[3])Alcohol C = triethylene glycol
[4])Alcohol D = 2-hydroxymethyl-2-methylpropanediol
[5])1:10 = reference, i.e. not crosslinked and not treated with alcohol

TABLE 2

| Sample No. | Temperature °C. | Diameter cm | Sheet pressure bar | Density kg/m3 at 2.5 kpa | Spec. vol. wet Dm3/kg at 2.5 kPa | Absorption capacity g/g | Relative density |
|---|---|---|---|---|---|---|---|
| 1:0:A | 90 | 5.40 | 6 | 96 | 10.07 | 9.80 | 100 |
| 1:0:B | 90 | 5.40 | 12 | 110 | 9.66 | 9.52 | 100 |
| 1:0:C | 90 | 5.45 | 26 | 157 | 8.72 | 8.38 | 100 |
| 1:0:D | 90 | 5.50 | 50 | 182 | 8.55 | 8.14 | 100 |
| 1:0:E | 130 | 5.50 | 50 | 285 | 8.03 | 7.60 | 100 |
| 1:2:A | 90 | 5.40 | 6 | 123 | 9.22 | 9.07 | 128 |
| 1:2:B | 90 | 5.45 | 12 | 140 | 8.93 | 8.69 | 128 |
| 1:2:C | 90 | 5.45 | 26 | 219 | 7.83 | 7.50 | 140 |
| 1:2:D | 90 | 5.50 | 50 | 224 | 8.50 | 8.10 | 123 |
| 1:2:E | 130 | 5.50 | 50 | 354 | 7.65 | 7.30 | 124 |
| 1:3:A | 90 | 5.50 | 6 | 132 | 8.64 | 8.37 | 137 |
| 1:3:B | 90 | 5.50 | 12 | 200 | 8.24 | 7.80 | 184 |
| 1:3:C | 90 | 5.40 | 26 | 230 | 7.69 | 7.45 | 147 |
| 1:3:D | 90 | 5.50 | 50 | 351 | 7.43 | 7.48. | 193 |
| 1:3:E | 130 | 5.45 | 50 | 471 | 6.92 | 6.70 | 166 |

TABLE 2-continued

| Sample No. | Temperature °C. | Diameter cm | Sheet pressure bar | Density kg/m3 at 2.5 kpa | Spec. vol. wet Dm3/kg at 2.5 kPa | Absorption capacity g/g | Relative density |
|---|---|---|---|---|---|---|---|
| 1:4:A | 90 | 5.40 | 6 | 104 | 9.52 | 9.28 | 108 |
| 1:4:B | 90 | 5.40 | 12 | 130 | 8.74 | 8.75 | 118 |
| 1:4:C | 90 | 5.45 | 26 | 146 | 8.16 | 7.82 | 93 |
| 1:4:D | 90 | 5.50 | 50 | 254 | 8.36 | 7.89 | 139 |
| 1:4:E | 130 | 5.50 | 50 | 340 | 7.86 | 7.00 | 119 |
| 1:5:A | 90 | 5.40 | 6 | 101 | 9.80 | 9.23 | 105 |
| 1:5:B | 90 | 5.50 | 12 | 124 | 9.02 | 8.76 | 113 |
| 1:5:C | 90 | 5.45 | 26 | 148 | 8.53 | 8.32 | 95 |
| 1:5:D | 90 | 5.50 | 50 | 185 | 8.50 | 7.98 | 101 |
| 1:5:E | 130 | 5.55 | 50 | 328 | 7.35 | 6.80 | 115 |
| 1:6:A | 90 | 5.40 | 6 | 176 | 8.17 | 7.61 | 183 |
| 1:6:B | 90 | 5.45 | 12 | 223 | 7.74 | 7.19 | 204 |
| 1:6:C | 90 | 5.50 | 25 | 270 | 7.31 | 7.04 | 172 |
| 1:6:D | 90 | 5.50 | 50 | 373 | 7.31 | 6.99 | 204 |
| 1:6:E | 130 | 5.50 | 50 | 463 | 6.65. | 6.30 | 163 |
| 1:10:A | 20 | 5.50 | 6 | 150 | 7.69 | 7.60 | |
| 1:10:B | 20 | 5.50 | 12 | 217 | 7.12 | 6.50 | |
| 1:10:C | 20 | 5.40 | 26 | 337 | 6.25 | 5.80 | |
| 1:10:D | 20 | 5.40 | 52 | 453 | 5.51 | 5.00 | |

Test pieces having a weight of 1 g and a diameter of 50 mm were formed in accordance with the above description. The test pieces were then compressed at different pressures and temperatures in a laboratory press using heated press plates. The true sheet pressure and resulting density were calculated after measuring the diameter and thickness of the compressed test piece.

The results which were obtained are shown in Table 2. The results in Table 2 have been illustrated in diagrammatic form in FIGS. 3–5. In these figures, the curves have been drawn using the corresponding data in Table 2. In addition, the concept of relative density has been introduced. The definition of this is as follows: pair-wise comparison of crosslinked pulp with pulp which was crosslinked in the presence of polyfunctional alcohol containing a corresponding quantity of crosslinking agent. The compression was carried out using the same conditions as regards pressure, temperature and time. The density of the pulp which was only crosslinked is then given the value of 100%.

Figure 3:
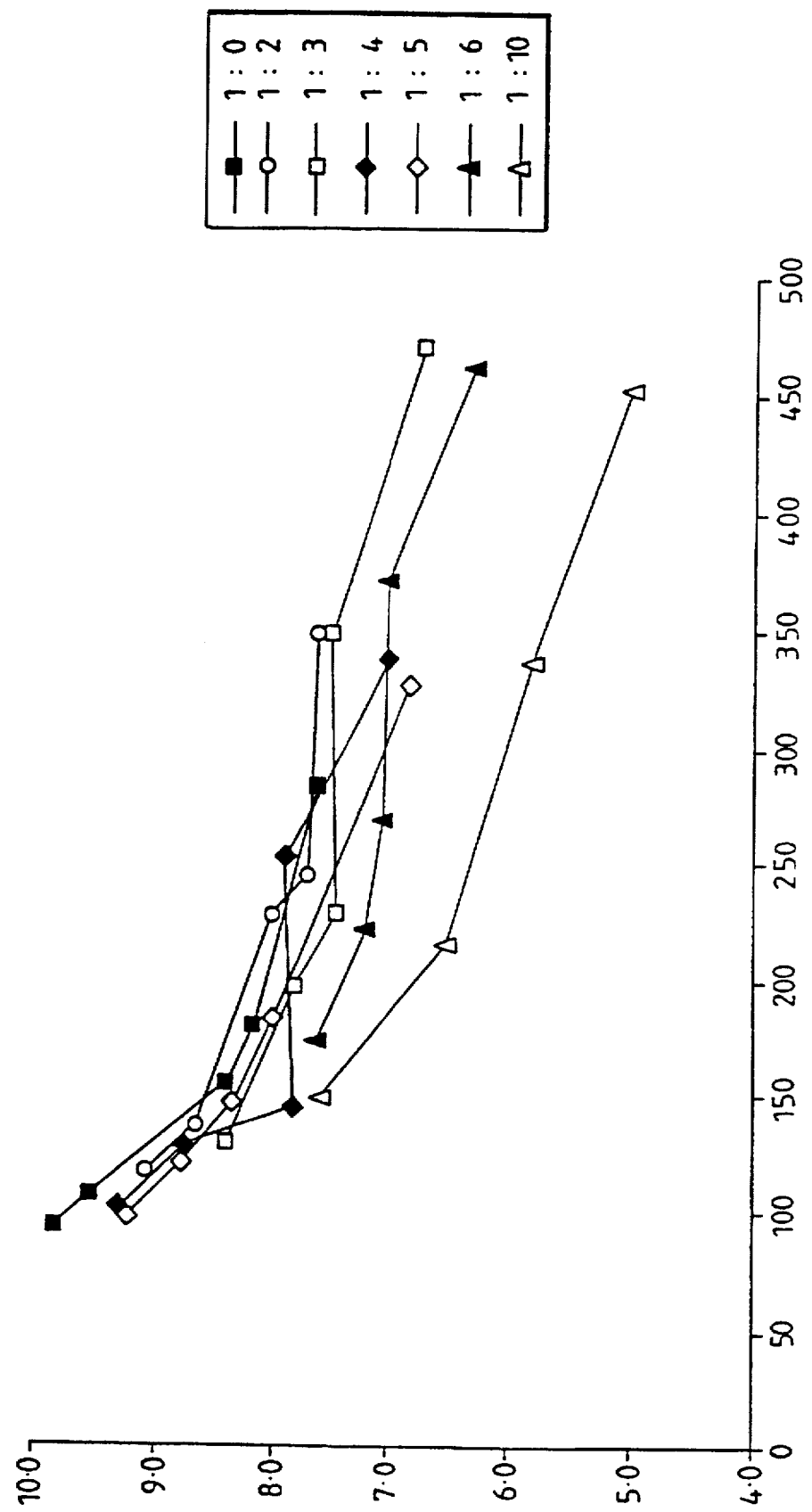
FIG. 3 shows the absorption capacity as a function of the initial density in the dry state when making measurements on compressed fluff pulp which has been crosslinked in the dry state.

FIG. 3 shows the absorption capacity as a function of the density in the dry state when carrying out measurements on dry-crosslinked, compressed fluff pulp. It is evident from this figure that the completely untreated fluff pulp (1:10, reference which was not crosslinked and not treated with alcohol) has the worst absorption capacity at all initial dry densities. It is also evident that the fluff pulp which was only crosslinked (1:0, which was not treated with alcohol) has an absorption capacity which is only marginally better than that of fluff pulp which was treated with alcohol in accordance with this invention (1:2, 1:3, 1:4, 1:5 and 1:6).

Figure 4:
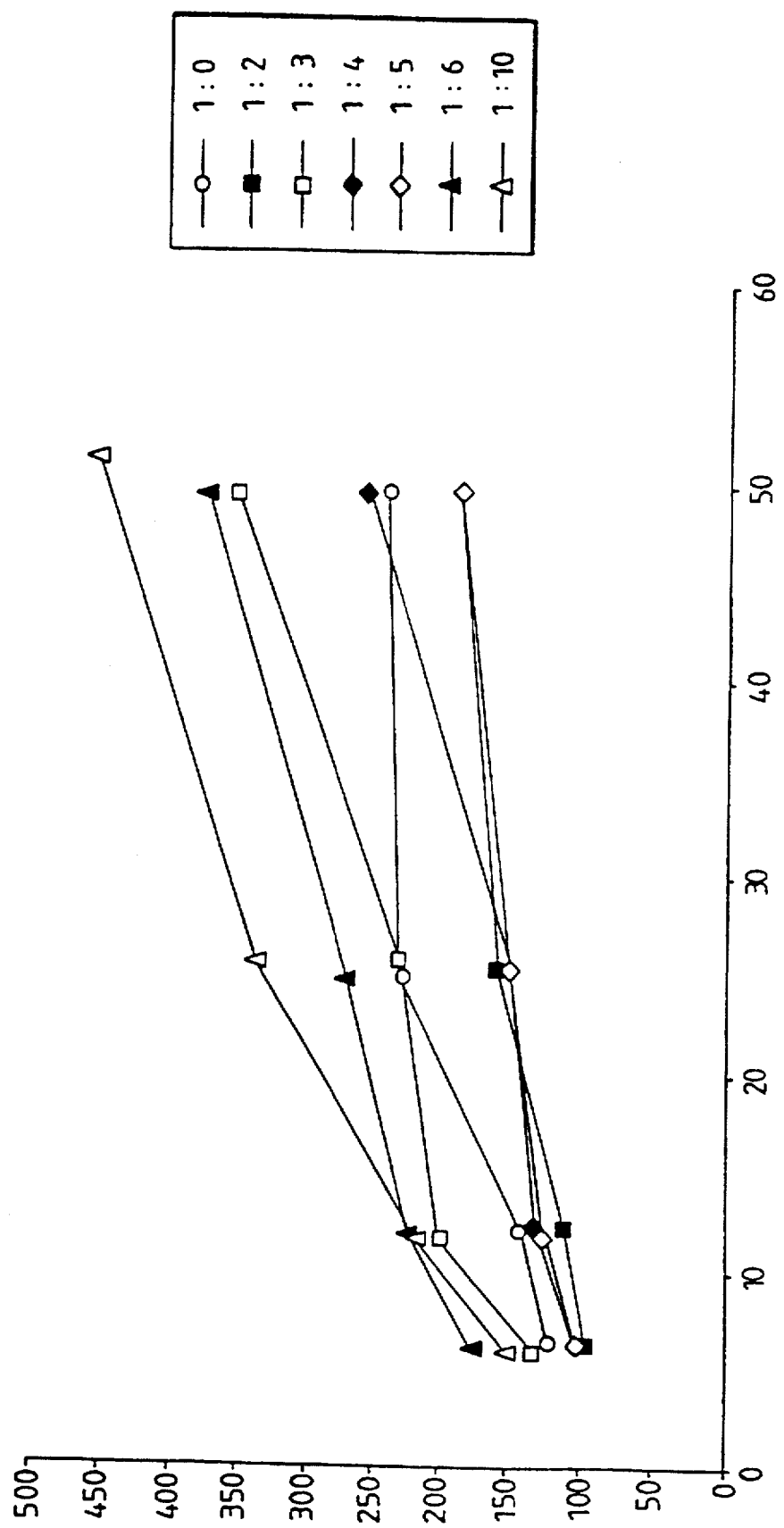
FIG. 4 shows the density as a function of the applied sheet pressure at 90° C. when compressing fluff pulp which has been crosslinked in the dry state.

FIG. 4 shows the density as a function of the applied sheet pressure when compressing, at 90° C., fluff pulp which was crosslinked in the dry state. The completely untreated fluff pulp (1:10) is most readily compressed, due to the fact that it is not crosslinked. Nevertheless, the crosslinked fluff pulp which was treated with triethylene glycol (1:5) has compression properties which are largely unchanged, showing that the chemical structure of the alcohols also has an effect on the result.

Figure 5:
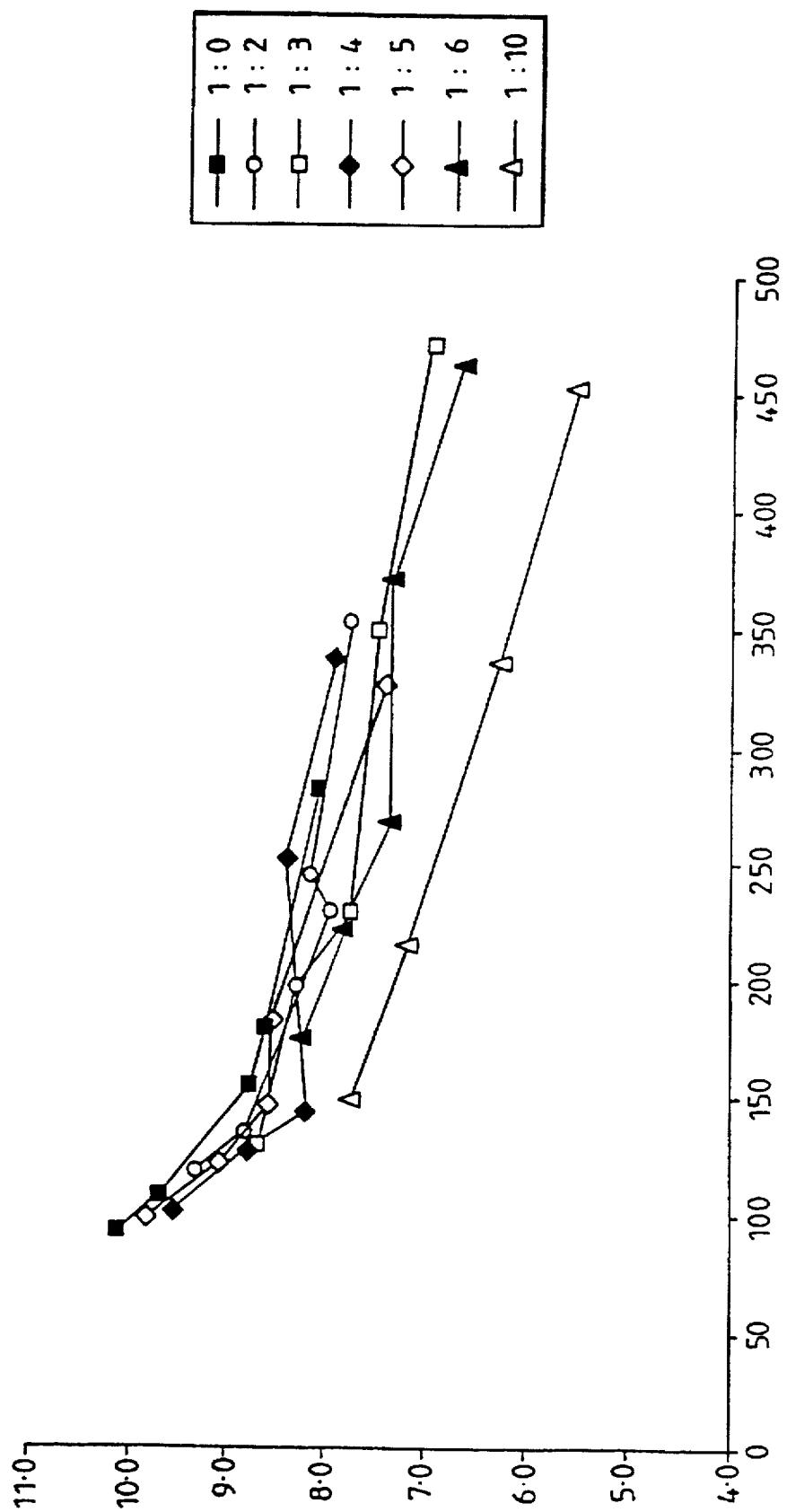
FIG. 5 shows the wet specific volume as a function of the initial density for compressed fluff pulp which has been crosslinked in the dry state.
Figure 6:
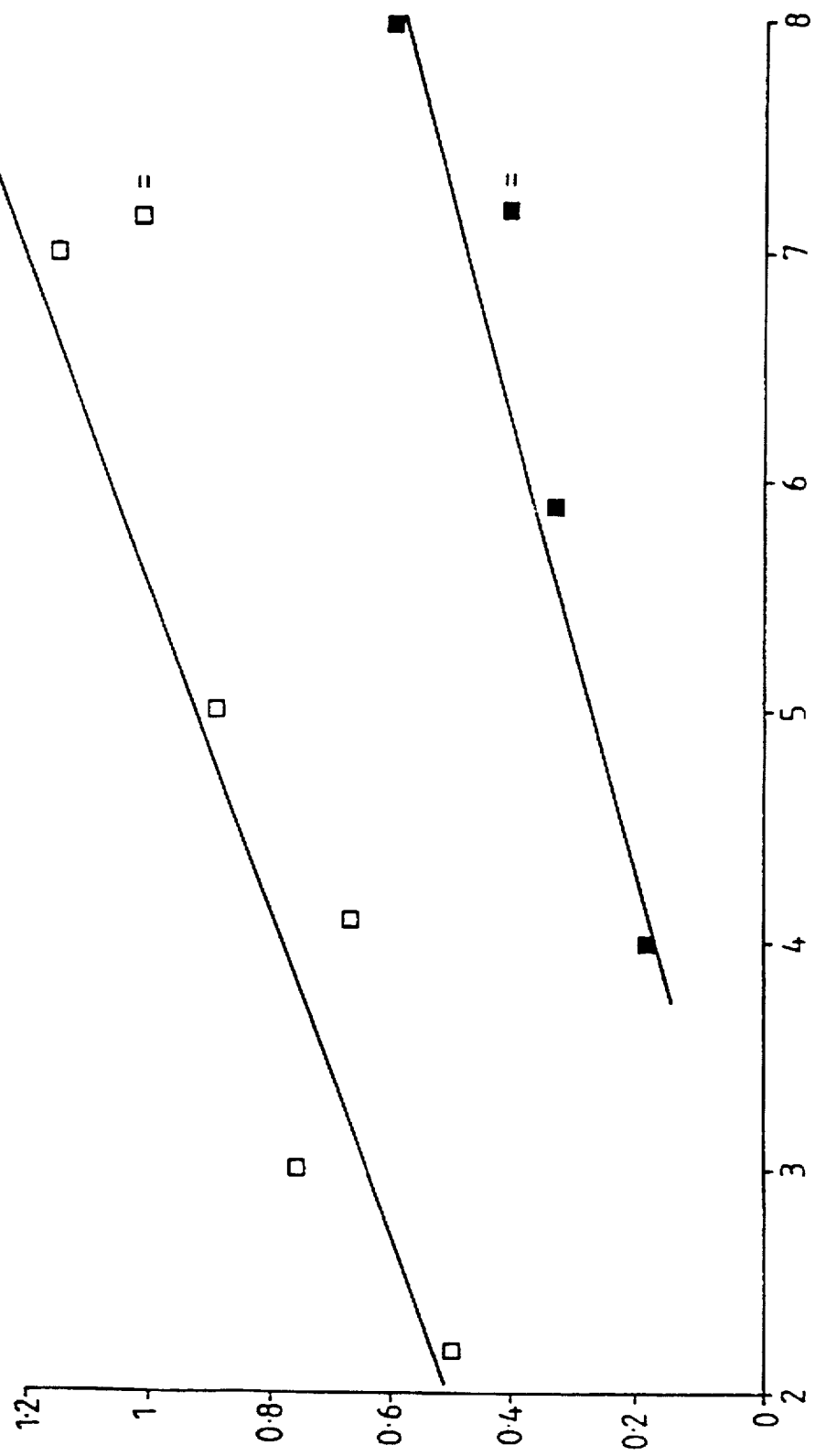
FIG. 6 shows, in the form of a diagram, the absorption rate as a function of the thickness of the test sample, firstly in a cellulose product according to the invention which has been supplied with superabsorbent powders (SAP), and secondly in a reference material which also contains superabsorbent of the same type, FIG. 7 constitutes a flow diagram which schematically illustrates a first preferred embodiment of the method for preparing fluff pulp, or other defibrated cellulose product, according to the invention, and FIG. 8 constitutes a flow diagram which schematically illustrates a second preferred embodiment of the method for preparing fluff pulp, or other defibered cellulose product, according to the invention.

FIG. 5 shows the wet specific volume as a function of the initial density in compressed fluff pulp which was crosslinked in the dry state. In this comparison, the completely untreated fluff pulp (1:10) cannot hold as much liquid as can the other fluff pulp samples. High wet specific volumes at high densities are found for the other fluff pulp samples which were treated with alcohol (1:2, 1:3, 1:4, 1:5 and 1:6). This is especially evident in samples 1:3 and 1:6 which, along the whole of the respective curves, have a wet specific volume which is equivalent to that of the untreated fluff pulp sample, at a density which is at least 50 kg/m3 higher.

EXPERIMENTAL SERIES 2

The function of the alcohols in decreasing resilience in the dry state has also been tested when using other crosslinking agents, such as a methyl derivative of dimethyldihydroxyethyleneurea, DMDHEU (commercial product from Société Francaise Hoechst and having the trade name Arkofix NZF), as is evident from Tables 3 and 4. Catalyst V3881 consists of an acidic solution (pH=0) of magnesium chloride and acetic acid. The concentrations which are given with regard to Arkofix NZF and catalyst V3881 relate to absolutely dry product after determining dry matter content in an incubator at 110° C. The procedure for carrying out Experimental series 2 is similar to the above described procedure in all respects apart from the fact that the reaction conditions for crosslinking with the said methyl derivative of dimethyldihydroxyethyleneurea (Arkofix NZF) are that the crosslinking takes place at 160° C. for 3 min.

TABLE 3

| Sample No. | Crosslinking agent Arkofix NZF* g/l | Catalyst V3881 g/l | Impregnating agent glycerol g/l | Amount applied g/kg |
|---|---|---|---|---|
| 2:1 | 59 | 2 | — | 50 |
| 2:2 | 59 | 2 | 59 | 99 |

*Trade name for methyl derivative of dimethyldihydroxy-ethyleneurea, DMDHEU

TABLE 4

| Sample No. | Temperature °C. | Diameter cm | Sheet pressure bar | Density kg/m3 at 2.5 kPA | Spec. vol. wet dm3/kg at 2.5 kPa | Absorption capacity g/g | Relative density % |
|---|---|---|---|---|---|---|---|
| 2:1:A | 90 | 5.50 | 25 | 156 | 8.41 | 7.9 | 100 |
| 2:1:B | 90 | 5.45 | 50 | 216 | 7.65 | 7.2 | 100 |
| 2:2:A | 90 | 5.45 | 25 | 367 | 6.67 | 6.0 | 235 |
| 2:2:B | 90 | 5.40 | 50 | 465 | 6.23 | 5.9 | 216 |

EXPERIMENTAL SERIES 3

An excess of aqueous solutions having the composition as given in Table 5 (remainder water) was added to a pulp web based on Nordic softwood sulphate pulp. The excess of the solution was pressed out in a single-felted press nip.

TABLE 5

| Sample No. | Cross-linking agent citric acid g/l | Catalyst NaH2PO4 g/l | Impregnating agent glycerol g/l | Dry matter content after pressing % | Calculated amount applied g/kg |
|---|---|---|---|---|---|
| 3:1 | 31 | 12 | — | 49.1 | 45 |
| 3:2 | 31 | 12 | 25 | 49.0 | 71 |
| 3:3 | 31 | 12 | 50 | 49.8 | 94 |
| 3:4 | 38 | 15 | 75 | 51.5 | 121 |
| 3:5 | 48 | 19 | 50 | 51.5 | 110 |
| 3:6 | 48 | 19 | — | 49.6 | 68 |

The moist web of cellulose fibre was torn in a toothed screw into pieces having a size of about 1 centimeter, which pieces were defibrated twice, without previous drying, in a 20-inch disc refiner. Immediately after the cellulose fibre had passed through the disc refiner in the second defibration stage the fibre, which had thus been substantially individualized, was dried by being dispersed in heated air. The cellulose fibre was dried from a dry content of approximately 50% to a dry content of approximately 90%. The crosslinking reaction was then initiated by heating the fibre material at 180° C. for 6 min.

The resulting cellulose product was then examined in the same way as in Experimental series 1 and 2. The results are given in Table 6.

TABLE 6

| Sample No. | Temperature °C. | Diameter cm | Sheet pressure bar | Density kg/m3 at 2.5 kpa | Spec. vol. wet dm3/kg at 2.5 kPa | Absorption capacity g/g | Relative density %- |
|---|---|---|---|---|---|---|---|
| 3:1:A | 90 | 5.60 | 24 | 175 | 10.41 | 10.0 | 100 |
| 3:1:B | 90 | 5.60 | 48 | 185 | 9.95 | 10.2 | 100 |
| 3:2:A | 90 | 5.55 | 25 | 230 | 9.29 | 9.1 | 131 |
| 3:2:B | 90 | 5.60 | 48 | 339 | 8.76 | 8.6 | 183 |
| 3:3:A | 90 | 5.55 | 25 | 254 | 8.97 | 8.6 | 145 |
| 3:3:B | 90 | 5.55 | 49 | 390 | 8.00 | 7.8 | 211 |
| 3:4:A | 90 | 5.60 | 24 | 336 | 8.25 | 8.1 | 192 |
| 3:4:B | 90 | 5.60 | 48 | 376 | 7.88 | 7.5 | 204 |
| 3:5:A | 90 | 5.60 | 24 | 208 | 9.01 | 8.8 | 188 |
| 3:5:B | 90 | 5.50 | 50 | 348 | 8.10 | 7.9 | 255 |

TABLE 6-continued

| Sample No. | Temperature °C. | Diameter cm | Sheet pressure bar | Density kg/m3 at 2.5 kpa | Spec. vol. wet dm3/kg at 2.5 kPa | Absorption capacity g/g. | Relative density %- |
|---|---|---|---|---|---|---|---|
| 3:6:A | 90 | 5.55 | 25 | 111 | 11.03 | 11.4 | 100 |
| 3:6:B | 90 | 5.55 | 49 | 136 | 10.42 | 10.1 | 100 |

It is evident from the above Tables and the attached Figure drawings 3–5 that the compressibility of a cellulose product which consists essentially of fibres which have been crosslinked in the dry state in the presence of bifunctional trifunctional or polyfunctional alcohols, and thereby gained the said structure of cellulose fibres, can be controlled by the amount and type of the said bifunctional, trifunctional or polyfunctional alcohols which are added.

When an alcohol is added, the cellulose product according to the invention, and its structure of cellulose fibres, are compressed to a substantially greater extent than is fluff pulp at the same compression pressure when this fluff pulp has only been crosslinked. At comparable initial dry densities, a cellulose fibre structure according to the invention and a cellulose fibre structure which is only crosslinked also have comparable absorption properties. While having a substantially higher dry density prior to wetting, a cellulose fibre structure according to the invention has an absorption capacity/wet specific volume which is as high as that of cellulose fibre structures which have not been crosslinked.

EXPERIMENTAL SERIES 4

Experimental series 4 was designed with the aim of reviewing further the possibilities for using the dry-crosslinked and compressed fibre in absorbent products, such as, for example, babies' nappies. More particularly, the aim of the experiments was to study absorption rate and its dependence on the thickness/degree of compression of the absorptive pad.

Present-day standard nappies are often packed at densities within the range 150–200 kg/m3. However, a certain spring-back takes place during use/evaluation. Reference samples, of which the reference material in sample No. 3, Table 7 below, can, in particular, be regarded as representing the absorptive pad in a baby's nappy of the modem type, as regards performance (absorption rate) and thickness, were included in the experimental series. An essential property of nappies is the rate with which the liquid is absorbed by the absorptive pad. A low rate of absorption results in an increased risk of leakage since the urine which is not absorbed promptly by the absorptive pad must be kept enclosed within the nappy by different forms of sealing functions. The absorption rate in association with the first dosing with liquid is judged not to be critical for current standard nappies. On the other hand, the decreased rate of absorption associated with increasing liquid loading entails an increasing risk of leakage.

A commercial fluff pulp, known under the trade name Stora Cell EC 0.1 (manufacturer, Stora Kopparbergs Bergslags AB), which is a sulphate fluff pulp based on Nordic softwood fibre, was used as the reference material. The pulp was defibrated at 3500 rpm in a Kamas HO1 hammer mill having an 8 mm sieve. Pads were formed with an air-laying technique using the defibrated material A superabsorbent (SAP) was used which is known under the trade name Drytech 510 (manufacturer Dow Chemical Corp.), which, according to information from the manufacturer, is defined as a crosslinked acrylate copolymer. The superabsorbent, Drytech 510 HC, was added to the pads at different levels in three additions. The pads were pressed in a press under the conditions of pressure and temperature given in Table 7. When being used for evaluating absorption rate, all the pads had the dimensions 12*30 cm but varied in thickness and density.

The novel fibre which was produced in accordance with Example 3:2, Table 5, was formed into sheets having a grammage of approximately 700 g/m2 and having the dimensions 12×30 cm The sheets were compressed at approximately 20 bar and at 130° C. for 30 s, resulting in a sheet density of approximately 400 kg/m3. The material was cut into strips of approximately 4.7 cm in width which were then defibrated at 2500 rpm in a Kamas HO1 laboratory mill having an 8 mm sieve. The fluffed material was subsequently formed into pads with an air-laying technique and superabsorbent, Drytech 510 HC, was distributed in the sheet by being added in three batches. The formed sheets were pressed in a press under the conditions of pressure and temperature given in Table 7. When being used for evaluating absorption rate, all the sheets had the dimensions 12×30 cm but varied in thickness and density.

As can be seen from Table 7 and diagram, an absorptive pad based on a conventional fluff pulp which has not been crosslinked loses, to a large extent, the important function of rapidly absorbing liquid if it has been compressed to high initial dry density or otherwise pressed out into a thin absorptive pad. By contrast, an absorptive pad based on the novel fibre can be compressed to a thickness which is less than half the thickness of for example, the reference sample 3, Table 7, while having an absorption rate which is largely maintained or, in several cases, even increased, when the test piece has been loaded with liquid, Le. in dosages 2–4. The results thus demonstrate that the novel fibre provides substantially improved possibilities for developing thin, but nevertheless functionally satisfactory, absorbent products having a high absorption rate, and thus also decreased leakage frequency, as compared with a chemical fluff pulp which contains a high proportion of superabsorbent and is only compressed and not crosslinked.

There are many options for varying the design of the absorptive pad. For example, the densities in different layers, the distribution and type of super-absorbent, the non-uniform grammage profile, etc. can be varied. All these aspects have an influence on absorption rate. The examples should thus not be seen as a limitation of the invention but are only intended to demonstrate differences in performance between a present-day commercial, chemical fluff pulp and the novel pulp when being used in thin, absorbent products, particularly when the absorptive pad has been compacted to a high density, i. e. >200 kg/m3.

TABLE 7

| Sample No. | | Reference | | Examples of absorptive pads according to the invention | | | | | |
|---|---|---|---|---|---|---|---|---|---|
| | | 1 | 2 | 3 | 4 | 5 | 6 | 7 | 8 |
| Pulp | | | Stora Cell | Stora Cell | Stora Cell | | | | | |
| | | | EC 0.1 | EC 0.1 | EC 0.1 | 3:2* | 3:2* | 3:2* | 3:2* | 3:2* |
| Surface weight value, target value | g/m2 | 1000 | 1000 | 1000 | 1000 | 1000 | 1000 | 1000 | 800 |
| Surface weight SAP**, target value | g/m2 | 140 | 140 | 140 | 140 | 140 | 140 | 140 | 140 |
| Pressing: | | | | | | | | | |
| Pressure | bar | 18.1 | 10.9 | 7.4 | 14.3 | 8.0 | 5.1 | 14.1 | 8.1 |
| Time | s | 40 | 20 | 30 | 40 | 15 | 10 | 80 | 12 |
| Temperature | °C. | 20 | 20 | 20 | 90 | 90 | 90 | 130 | 90 |
| Sample weight incl. SAP (12*30) | g | 41.6 | 41.8 | 41.9 | 41.6 | 42.2 | 42.0 | 42.5 | 36.3 |
| Quantity of SAP | g | 5 | 5 | 5 | 5 | 5 | 5 | 5 | 5 |
| Surface weight, (fluff + SAP) | g/m2 | 1202 | 1206 | 1234 | 1152 | 1164 | 1153 | 1159 | 993 |
| Thickness (") | mm | 4.0 | 5.9 | 8.0 | 3.0 | 5.0 | 7.0 | 2.2 | 4.1 |
| Density (") | kg/m3 | 297 | 205 | 154 | 381 | 235 | 165 | 539 | 242 |
| Absorption rate -: | 4 × 50 ml | | | | | | | | |
| Dosage 1 | ml/s | 0.91 | 2.32 | 5.75 | 1.85 | 2.44 | 4.68 | 1.37 | 2.18 |
| Dosage 2 | ml/s | 0.37 | 0.68 | 1.49 | 1.38 | 1.57 | 2.08 | 1.03 | 1.31 |
| Dosage 3 | ml/s | 0.26 | 0.45 | 0.86 | 1.08 | 1.15 | 1.42 | 0.76 | 0.96 |
| Dosage 4 | ml/s | <0.18 | 0.33 | 0.59 | 0.76 | 0.89 | 1.15 | 0.50 | 0.67 |

DESCRIPTION OF INDUSTRIAL EMBODIMENTS

Figure 7:
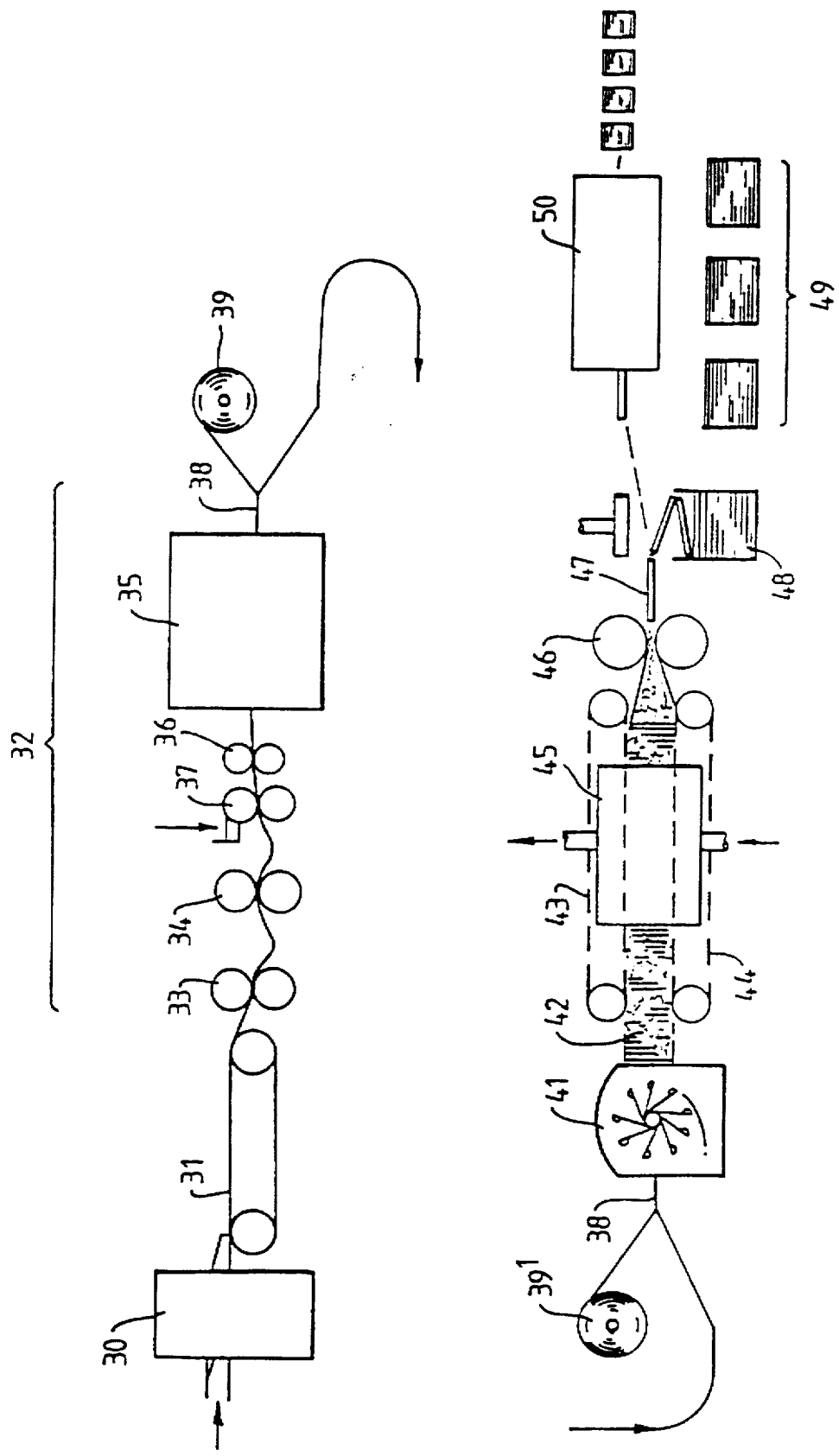

FIG. 7 schematically illustrates a first method of implementing the invention in fill scale in continuously operating processes. The upper part of the schematic flow diagram in FIG. 7 illustrates how and where the crosslinking chemicals as well as the alcohols according to this invention can be added to the process, in accordance with one example, and the lower part of the flow diagram shows the subsequent preparation, comprising defibration and crosslinking.

A furnish is pumped through a headbox 30 out onto a wire section 31. A press section has been generally designated 32.

The press section comprises a number of presses 33, 34 and a dryer 35. The press section 32 can also contain several presses upstream and downstream of the dryer 35, which can also be termed a pre-dryer.

The crosslinking reagent and alcohols which are used in accordance with the invention, together with catalyst(s), are added, in accordance with the preferred embodiment, to the web-shaped cellulose sheet before the latter is dried, expediently in the press section at a point in the process when the pulp has a dry content amounting to at least 20%, expediently a dry matter content in the range 30–50%. Different methods and arrangements are conceivable for applying the chemicals so that they are efficiently incorporated into the pulp material. For example, the chemical solution can conceivably be sprayed onto the pulp from one or more transverse sprinkler pipes and integration of the chemicals into the pulp subsequently effected using a downstream press 36. Preferably, however, the chemicals are expediently supplied using an apparatus 37 of the type which is conventionally used as a size press, this being a well-tried technique for incorporating chemicals into relatively thick and bulky sheets. The web material, which now contains the chemicals, is dried in the dryer 35 at a temperature below the crosslinking temperature of the chemicals, preferably at a web temperature of less than 100° C.

After the dryer 35, the web-shaped sheet 38 can be reeled up into roller bales 39 or—alternatively—conducted directly to a plant for defibering and hardening. This unit has been designated 40 in FIG. 7. The web material 38 is next conducted into a defibrator 41. An apparatus which is suitable for dry defibration is a hammer mill, which is available in different designs. Other equipment, for example disc refiners, are also conceivable in principle for bringing about dry defibration, but a hammer mill is to be preferred in relation to dry defibration.

As a result of being defibrated in the apparatus 41, the material is fluffed and consequently achieves a high specific volume. At the same time, it also loses most of its fibre-binding properties and is therefore difficult to re-shape into an interconnected web. However, it is desirable to be able to carry out the crosslinking, which follows the defibration, under continuous conditions, which permit regulation of the crosslinking time and crosslinking temperature, and which simultaneously ensure that the pulp is treated uniformly in all parts of the bulky, fluffed material. According to a preferred embodiment, the fluffed pulp 42 is fed in between two endless, relatively wide-apart, wires 43, 44. The fluffed pulp 42 is, as it were, confined in between the wires 43, 44 and is fed slowly through a tunnel oven 45. Warm gas flows through the oven 45. By means of adjusting the feeding speed of the wires 43, 44, the dwell time of the pulp 42 in the oven 45 at reaction temperature is expediently regulated to be between 1 and 30 min, preferably to be between 2–10 min. The temperature in the oven is regulated to between 100° and 210° C., preferably to be greater than 120° C., expediently to be between 140° and 190° C., in association with which the added chemicals are activated and initiate the intended reactions with the cellulose molecules. After treatment in the oven 45, the pulp is expediently cooled, which can be carried out in a separate cooling zone.

The material which has been prepared in this way is then pressed together once again in a press 46 to form a more or less interconnected material 47, which is folded and baled in a baling press 48. The finished bales have been designated 49. Alternatively, the material 47 can be conveyed directly to a nappy manufacturing plant 50 or to a plant for manufacturing other absorbent products. This plant can in principle be connected directly after the oven 45, thereby eliminating the need for additional fluffing. As a further alternative, the material can be rolled into rolls (not shown), as has been mentioned above.

Figure 8:
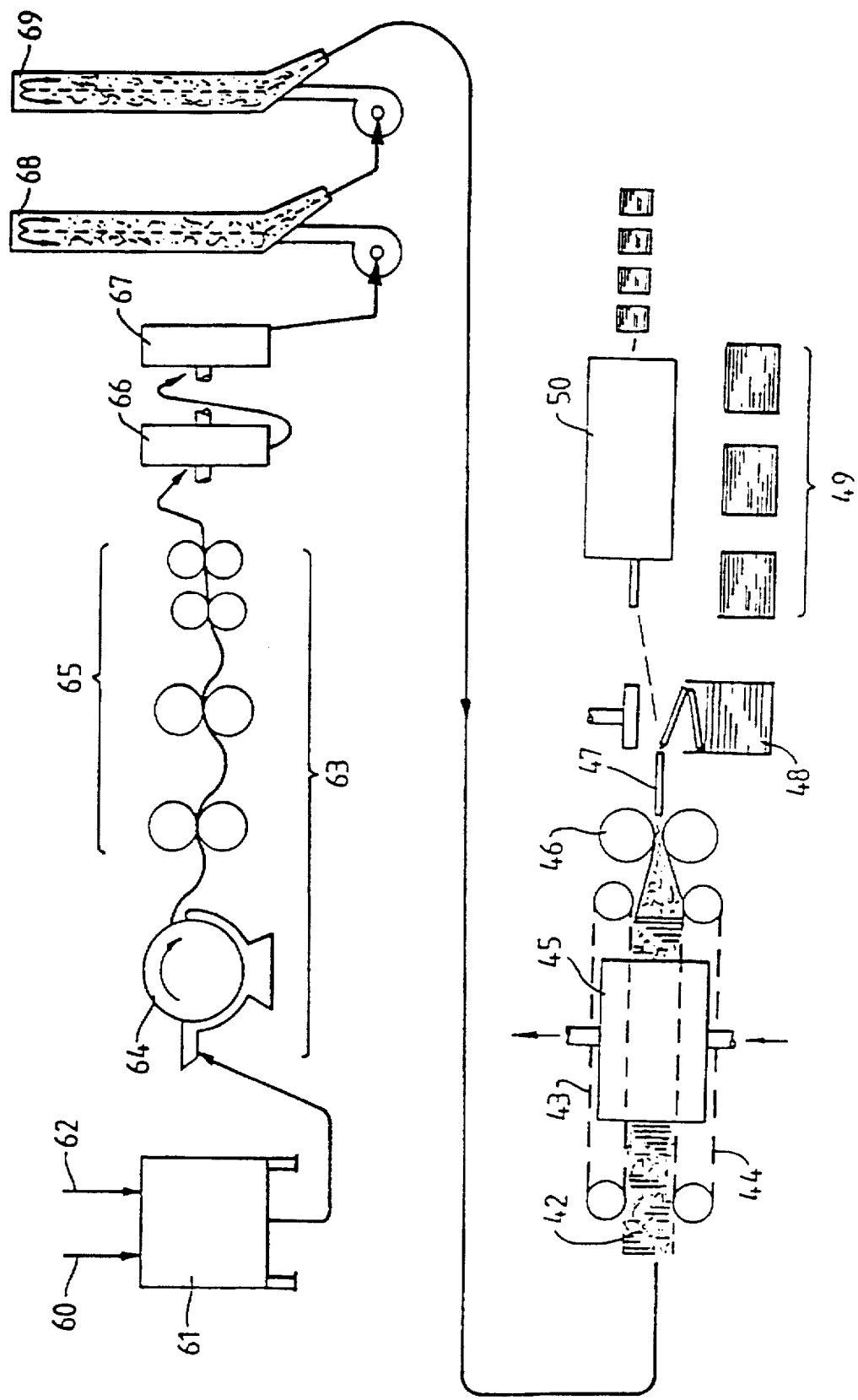

FIG. 8 schematically illustrates a second method of implementing the invention in full scale in continuously operating processes. Roll or bale pulp 60 is conveyed to a disintegrator, a so-called pulper 61, where the pulp 60 is dispersed in water 62, which contains the relevant chemicals. The slurry which is obtained in this way is dewatered. This can be effected, for example, in a thickener, designated generally by 63. In the example, the thickener contains, in a conventional manner, a suction cylinder wire 64 and a press section 65. A predryer may also be present. The dewatering gives rise to a so-called wet pulp which has a dry content of 45–50%. The wet pulp is defibrated in disc refiners 66, 67 and is then dried in a flash dryer 68 at a fibre temperature of less than 100° C. and is finally heated in a further tower 69 in order to be thoroughly heated homogeneously immediately before the activation of the crosslinking chemicals, which can be carried out in the manner which has been described in association with the preceding examples. This part of the process, comprising treatment in the units 42–50, will not therefore be described in any further detail here, and reference will simply be made to the preceding description.

It will be evident that the above described industrial embodiments only constitute examples of how the invention can be implemented on an industrial scale. Thus, the chemicals might, instead, very well be added after the defibering. Nor is it necessary to add the chemicals in one and the same solution, or even at the same time in the process. The sequence in which the different chemicals—crosslinking reagent, catalyst and the said alcohols or their equivalent—are added is probably not, therefore, of any crucial importance. The important thing is that the chemicals are present in the defibered cellulose pulp when the crosslinking reaction is initiated.

I claim:
1. Method for preparing a crosslinked cellulose product having good compressibility under the influence of heat and pressure in combination with good absorption properties, said method comprising the steps of:
   impregnating cellulose fibers with a crosslinking agent and at least one polyfunctional alcohol;
   drying the impregnated cellulose fibers
   defibrating said cellulose fibers to obtain defibrated cellulose fibers; and
   crosslinking said defibrated cellulose fibers in the dry state at a temperature of at least 110° C.
2. Method according to claim 1, wherein the crosslinking reaction is carried out in the dry state at a fiber temperature of between 140° and 190° C.
3. Method according to claim 1, wherein impregnation of the cellulose fibers with said polyfunctional alcohol causes the fibers to swell and soften.
4. Method according to claim 1, wherein said polyfunctional alcohol has a molecular weight which exceeds 60 g/mole.
5. Method according to claim 1, wherein said polyfunctional alcohol contains one or more heteroatoms selected from the group consisting of oxygen and nitrogen.
6. Method according to claim 1, wherein said polyfunctional alcohol contains one or two polar, functional groups selected from the group consisting of aldehyde groups, keto groups and carboxyl groups.
7. Method according to claim 1, wherein the cellulose fibers are impregnated with 2–150 g of said polyfunctional alcohol.

8. Method according to claim 1, wherein the cellulose fibers are impregnated with 5-50 g of said polyfunctional alcohol.

9. Method according to claim 1, wherein the cellulose fibers are impregnated with glycerol.

10. Method according to claim 1, wherein crosslinking reagent is added in an amount corresponding to 10-150 g of crosslinking agent/kg of cellulose fiber.

11. Method according to claim 1, wherein crosslinking reagent is added in an amount corresponding to 20-60 g of crosslinking agent/kg of cellulose fiber.

12. Method according to any of claim 1, wherein the cellulose fibers which are subjected to crosslinking are selected from among the group consisting of bleached, partially bleached and unbleached, sulphate-delignified or sulphite-delignified, softwood and hardwood fibers, thermomechanical and chemothermomechanical pulps bleached softwood sulphate pulp, and mixtures of said materials.

13. Method according to claim 1, wherein said crosslinking agent is selected from the group consisting of polyfunctional organic acids, polyfunctional aldehydes and heterocyclic compounds which have at least two nitrogen atoms in the ring in addition to carbon.

14. Method according to claim 13, wherein said crosslinking substance is selected from the group consisting of dihydroxyethyleneurea, dimethyl-dihydroxyethyleneurea, and derivatives thereof.

15. Method according to claim 1, wherein the crosslinking reaction is catalyzed by a substance selected from the group consisting of alkali metal hypophosphite, alkali metal polyphosphate, alkali metal phosphate, alkali metal sulphate, sodium fluoroborate, disodium carbonate, a Lewis acid and an organic amine.

16. Method according to claim 15, wherein said Lewis acid is iron trichloride.

* * * * *